(12) United States Patent
Brandt et al.

(10) Patent No.: US 9,127,009 B2
(45) Date of Patent: Sep. 8, 2015

(54) PREPARATION OF NORMORPHINANS

(71) Applicant: MALLINCKRODT LLC, Hazelwood, MO (US)

(72) Inventors: John Brandt, St. Charles, MO (US); Subo Liao, Ballwin, MO (US); Edmund C. Hudson, Clayton, MO (US); Esa T. Jarvi, Ballwin, MO (US); Peter X. Wang, Creve Coeur, MO (US); Michael Schaefer, St. Louis, MO (US)

(73) Assignee: Mallinckrodt LLC, Hazelwood ( * ) Notice: Subject to any disclaimer, the term of this patent is extended or adjusted under 35 U.S.C. 154(b) by 0 days.

(21) Appl. No.: 14/546,617

(22) Filed: Nov. 18, 2014

(65) Prior Publication Data

US 2015/0141649 A1    May 21, 2015

Related U.S. Application Data

(60) Provisional application No. 61/905,312, filed on Nov. 18, 2013.

(51) Int. Cl.
*C07D 489/02* (2006.01)
*C07D 489/12* (2006.01)

(52) U.S. Cl.
CPC .................... *C07D 489/02* (2013.01)

(58) Field of Classification Search
USPC ............................... 546/44, 45, 39
See application file for complete search history.

(56) References Cited

U.S. PATENT DOCUMENTS 7,671,204 B2 * 3/2010 Wang et al. .............. 546/46
8,101,757 B2    1/2012 Wang et al.
8,624,030 B2 * 1/2014 Wang et al. .............. 546/45
8,703,949 B2    4/2014 Liao et al.
2011/0015219 A1   1/2011 Trawick et al.
2012/0035367 A1   2/2012 Liao et al.

FOREIGN PATENT DOCUMENTS

WO    2009078990 A1    6/2009
WO    2009122436 A2   10/2009

OTHER PUBLICATIONS

Abdel-Monem et al., N-Demethylation of morphine and structurally related compounds with chloroformate ester, J. Medicinal Chem, 1972, pp. 208-210, vol. 15, No. 2.
Hobson et al., Cleavage of tertiary bases with phenyl chloroformate: The reconversion of 21-deoxyajmaline into ajmaline, J Chem Soc C, 1967, pp. 2015-2017.
Jacquemard, et al., Mild and selective deprotection of carbamates with Bu4NF. Tetrahedron, 2004, pp. 10039-10047, vol. 60, No. 44.
Rice, An improved procedure of the n-demethylation of 6,7-benzomorphans, morphine, and codeine, J Org Chem, 1975, pp. 1850-1851, vol. 41, No. 12.
Rice et al., Procedural refinements in the N-demethylation of morphine and codeine using phenyl chloroformate and hydrazine, J Heterocyclic Chem., 1977, p. 665-666, vol. 14.
Routier, et al., A mild and selective method for N-Boc deprotection, Tetrahedron Let, 2002, pp. 589-591, vol. 43. No. 4.
Wenkert et al., Short synthesis of eburnamonine via β-oxycyclopropylcarbonyl and related intermediates. J Am Chemical Soc, 1978, pp. 4893-4894, vol. 100, No. 15.
International Search Report and Written Opinion for related Application No. PCT/US2014/066152 dated Feb. 23, 2015, 8 pgs.

* cited by examiner

*Primary Examiner* — Charanjit Aulakh

(57) ABSTRACT

The present invention provides processes for preparing normorphinans from N-substituted morphinans. In particular, the invention provides methods for removing the N-substituent from the N-substituted morphinan to from a normorphinan carbamate, and then removing the carbamate functionality from the normorphinan carbamate to form the normorphinan.

17 Claims, No Drawings

PREPARATION OF NORMORPHINANS

CROSS-REFERENCE TO RELATED APPLICATIONS

This application claims the priority of U.S. provisional application Ser. No. 61/905,312, filed Nov. 18, 2013, which is hereby incorporated by reference in its entirety.

FIELD OF THE INVENTION

The present invention generally relates to the preparation of normorphinans from N-substituted morphinans.

BACKGROUND OF THE INVENTION

Normorphinans, which contain NH groups, are key intermediates for synthesizing important opioids such as naltrexone, naloxone, nalbuphine, nalmefene, and buprenorphine. Typically, normorphinans are prepared by the N-demethylation of N-methyl morphinans such as morphine, hydrocodone, or oxycodone. For this, the N-methyl morphinan generally is reacted with a hydrocarbyl chloroformate to form a normorphinan carbamate. Such demethylation reactions, however, tend to be unreliable, e.g., often failing to go to completion and requiring large excesses of the chloroformate and an added insoluble base. Thus, there is a need for more reliable and more efficient demethylation reactions during the preparation of normorphinans.

The preparation of normorphinans further comprises hydrolysis of the normorphinan carbamate to form the normorphinan. While carbamates can be readily hydrolyzed under acidic conditions, it is often necessary to conduct the hydrolysis under basic conditions in order to preserve acid sensitive functionalities, such as enol ethers, which may be present in the morphinan structure. The hydrolysis at high pH values requires high temperatures, typically above the boiling point of water at atmospheric pressure, which requires the use of pressurized reaction vessels made of corrosion-resistant material. Accordingly, there is a need for milder hydrolysis conditions (i.e., neutral pH levels, lower temperatures) for the removal of the carbamate functionality during the preparation of normorphinans.

SUMMARY OF THE INVENTION

Briefly, therefore, one aspect of the present disclosure encompasses a process for preparing a normorphinan from an N-substituted morphinan. The process comprises (a) contacting the N-substituted morphinan with a hydrocarbyl haloformate and a hindered tertiary amine to form an N-hydrocarboxycarbonyl morphinan and (b) contacting the N-hydrocarboxycarbonyl morphinan with a hydrolysis agent to form the normorphinan.

Another aspect of the disclosure provides a process for preparing a compound comprising Formula (III) from a compound comprising Formula (I). The process comprises (a) contacting a compound comprising Formula (I) with a hydrocarbyl haloformate, $XC(O)OR^{18}$, and a hindered tertiary amine to form a compound comprising Formula (II), and (b) contacting the compound comprising Formula (II) with a hydrolysis agent to form the compound comprising Formula (III) according to the following reaction scheme:

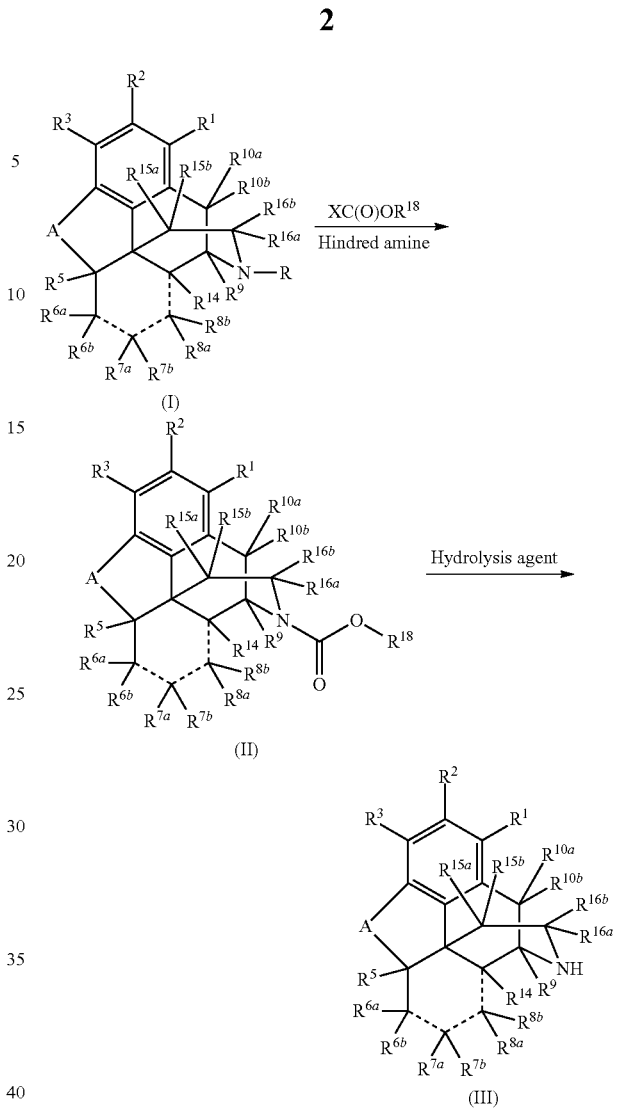

wherein:
A is oxygen, sulfur, or nitrogen;
R is hydrocarbyl or substituted hydrocarbyl;
$R^1$, $R^2$, and $R^3$ are independently hydrogen, amino, halogen, {—}OH, {—}$OR^{1611}$, {—}SH, {—}$SR^{1611}$, {—}$NHR^{1611}$, {—}$NR^{1611}R^{1612}$, hydrocarbyl, or substituted hydrocarbyl;
$R^5$, $R^{6a}$, $R^{6b}$, $R^{7a}$, $R^{7b}$, $R^{8a}$ $R^{8b}$, $R^9$, $R^{10a}$, $R^{10b}$, $R^{14}$, $R^{15a}$, $R^{15b}$, $R^{16a}$, and $R^{16b}$ are independently hydrogen, amino, halogen, {—}OH, {—}$OR^{1611}$, {—}SH, {—}$SR^{1611}$, {—}$NHR^{1611}$, {—}$NR^{1611}R^{1612}$, hydrocarbyl, or substituted hydrocarbyl; wherein any pair of $R^{\#a}$ and $R^{\#b}$ wherein # is any one of 6, 7, 8, 10, 15, 16, optionally together form a moiety chosen from {=}O, {=}S, {=}$CH_2$, {=}$NR^{1612}$; or {—}$O(CH_2)_nO${—}, wherein n is an integer of 1 or greater;
$R^{18}$ is hydrocarbyl or substituted hydrocarbyl
$R^{1611}$ and $R^{1612}$ are independently hydrocarbyl or substituted hydrocarbyl;
X is halogen;
one or more of $R^1$, $R^2$, $R^3$, $R^5$, $R^{6a}$, $R^{6b}$, $R^{7a}$, $R^{7b}$, $R^{8a}$ $R^{8b}$, $R^9$, $R^{10a}$, $R^{10b}$, $R^{14}$, $R^{15a}$, $R^{15b}$, $R^{16a}$, and $R^{16b}$ optionally forms part of a ring or ring system chosen from carbocyclic, substituted carbocyclic, heterocyclic, substituted heterocyclic, or a combination thereof; and the dashed lines between the carbon atoms at positions 6 and 7, 7 and 8, and 8 and 14 represent carbon to carbon bonds chosen from (a) single bonds between all carbon atoms, wherein optionally one of the $R^6$ pair and $R^{14}$ form an alkano bridge; (b) single bonds between the carbons at both positions 7 and 8 and 8 and 14, and a double bond between the carbons at positions 6 and 7, wherein only one of $R^6$ pair is present; (c) single bonds between the carbons at both positions 6 and 7 and 8 and 14, and a double bond between the carbons at positions 7 and 8, wherein only one of each $R^7$ and $R^8$ pair is present; or (d) double bonds between the carbons at both positions 6 and 7 and 8 and 14, and a single bond between the carbons at positions 7 and 8, wherein only one of each $R^6$, $R^7$, and $R^8$ pair is present and $R^{14}$ is not present.

Other features and iterations of the invention are described in more detail below.

DETAILED DESCRIPTION OF THE INVENTION

Disclosed herein are processes for preparing normorphinans. The processes comprise contacting an N-substituted morphinan with a hydrocarbyl halofomate and a proton acceptor to form a normorphinan carbamate. In some embodiments, the proton acceptor is a sterically hindered tertiary amine. The use of a hindered tertiary amine, either alone or in combination with a proton acceptor, such as inorganic salt, increases the rate and efficiency of the reaction. The carbamate functionality is removed from the normorphinan carbamate by contact with a hydrolysis agent to form the normorphinan. In some embodiments, the hydrolysis agent is a quaternary ammonium salt such that the hydrolysis reaction is performed under neutral conditions. In other embodiments, the hydrolysis agent is nucleophile (e.g., an alkali metal hydroxide) and the reaction is performed in the presence of a nucleophilic catalyst and/or a phase transfer agent thereof such that the reaction is conducted at a lower temperature than when no nucleophilic catalyst and/or phase transfer agent is present.

(I) Process for Preparation of Normorphinans

One aspect of the disclosure encompasses a process for preparing a normorphinan from an N-substituted morphinan. The process comprises removing the N-substituent by contacting the N-substituted morphinan with a hydrocarbyl haloformate and a proton acceptor to form an N-hydrocarboxycarbonyl morphinan, and (b) contacting the N-hydrocarboxycarbonyl morphinan with a hydrolysis agent to form the normorphinan. The proton acceptor may be a hindered tertiary amine, an inorganic salt, or a combination thereof; and the hydrolysis agent may be a quaternary ammonium salt, a nucleophile, or a combination thereof. The reactant mixtures and reaction conditions for each step of the process are detailed below in section (II).

In general, the morphinans and normorphinans detailed herein include any compound comprising a morphinan structure as diagrammed below, wherein R is hydrocarbyl or substituted hydrocarbyl in morphinans, and R is hydrogen in normorphinans. For the purposes of illustration, the ring atoms of the core morphinan structure are numbered as shown below:

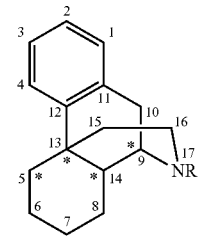

Morphinan compounds have asymmetric centers. In particular, the core morphinan compound may have at least four chiral carbons (designated by asterisks in the diagram above); namely, C-5, C-13, C-14, and C-9.

(II) Process for Preparing Compounds Comprising Formula (III) from Compounds Comprising Formula (I)

Another aspect of the disclosure provides a process for preparing a compound comprising Formula (III) from a compound comprising Formula (I). The process comprises contacting the compound comprising Formula (I) with a hydrocarbyl haloformate, $XC(O)OR^{18}$, and a proton acceptor chosen from a hindered tertiary amine and/or an inorganic salt to form a compound comprising Formula (II). The process further comprises contacting the compound comprising Formula (II) with a hydrolysis agent to form the compound comprising Formula (III). For purposes of illustration, Reaction Scheme 1 depicts the synthesis of the compound comprising Formula (III) in accordance with this aspect of the disclosure:

Reaction Scheme 1:

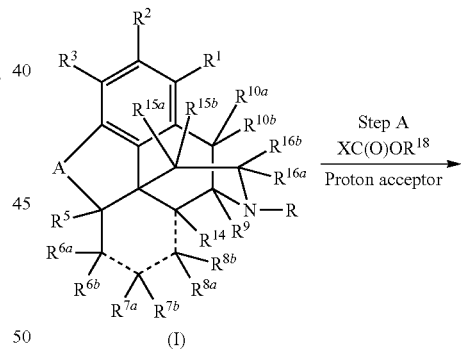

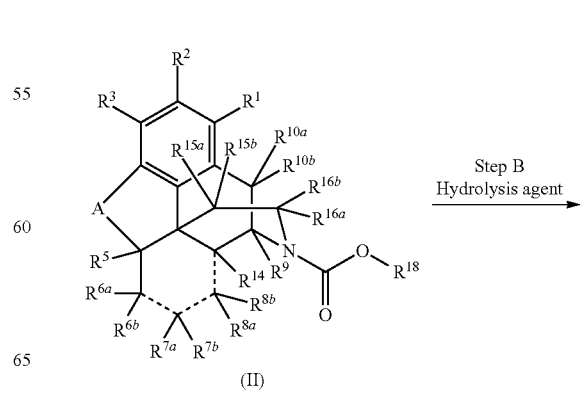

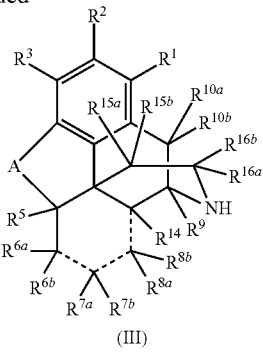

(III)

wherein:
A is oxygen, sulfur, or nitrogen;
R is hydrocarbyl or substituted hydrocarbyl;
$R^1$, $R^2$, and $R^3$ are independently hydrogen, amino, halogen, {—}OH, {—}$OR^{1611}$, {—}SH, {—}$SR^{1611}$, {—}$NHR^{1611}$, {—}$NR^{1611}R^{1612}$, hydrocarbyl, or substituted hydrocarbyl;
$R^5$, $R^{6a}$, $R^{6b}$, $R^{7a}$, $R^{7b}$, $R^{8a}$ $R^{8b}$, $R^9$, $R^{10a}$, $R^{10b}$, $R^{14}$, $R^{15a}$, $R^{15b}$, $R^{16a}$, and $R^{16b}$ are independently hydrogen, amino, halogen, {—}OH, {—}$OR^{1611}$, {—}SH, {—}$SR^{1611}$, {—}$NHR^{1611}$, {—}$NR^{1611}R^{1612}$, hydrocarbyl, or substituted hydrocarbyl; wherein any pair of $R^{\#a}$ and $R^{\#b}$ wherein # is any one of 6, 7, 8, 10, 15, 16, optionally together form a moiety chosen from {=}O, {=}S, {=}$CH_2$, {=}$NR^{1612}$; or {—}$O(CH_2)_nO${—}, wherein n is an integer of 1 or greater;
$R^{18}$ is hydrocarbyl or substituted hydrocarbyl
$R^{1611}$ and $R^{1612}$ are independently hydrocarbyl or substituted hydrocarbyl;
X is halogen;
one or more of $R^1$, $R^2$, $R^3$, $R^5$, $R^{6a}$, $R^{6b}$, $R^{7a}$, $R^{7b}$, $R^{8a}$ $R^{8b}$, $R^9$, $R^{10a}$, $R^{10b}$, $R^{14}$, $R^{15a}$, $R^{15b}$, $R^{16a}$, and $R^{16b}$ may form part of a ring or ring system chosen from carbocyclic, substituted carbocyclic, heterocyclic, substituted heterocylic, or combinations thereof; and
the dashed lines between the carbon atoms at positions 6 and 7, 7 and 8, and 8 and 14 represent carbon to carbon bonds chosen from (a) single bonds between all carbon atoms, wherein optionally one of the $R^6$ pair and $R^{14}$ form an alkano bridge; (b) single bonds between the carbons at both positions 7 and 8 and 8 and 14, and a double bond between the carbons at positions 6 and 7, wherein only one of the $R^6$ pair is present; (c) single bonds between the carbons at both positions 6 and 7 and 8 and 14, and a double bond between the carbons at positions 7 and 8, wherein only one of each $R^7$ and $R^8$ pair is present; or (d) double bonds between the carbons at both positions 6 and 7 and 8 and 14, and a single bond between the carbons at positions 7 and 8, wherein only one of each $R^6$, $R^7$, and $R^8$ pair is present and $R^{14}$ is not present.

In one embodiment, A is oxygen. In another embodiment, $R^1$, $R^2$, $R^3$, $R^5$, $R^{6a}$, $R^{6b}$, $R^{7a}$, $R^{7b}$, $R^{8a}$, $R^{8b}$, $R^9$, $R^{10a}$, $R^{10b}$, $R^{14}$, $R^{15a}$, $R^{15b}$, $R^{16a}$, and $R^{16b}$, if present, are independently hydrogen, halogen, hydroxyl, alkoxy, acyl, alkyl, alkenyl, aryl, substituted alkyl, substituted alkenyl, or substituted aryl. In a further embodiment, R and $R^{18}$ are independently alkyl, alkenyl, aryl, substituted alkyl, substituted alkenyl, substituted alkynyl, or substituted aryl.

In exemplary embodiments, A is oxygen, R is methyl, ethyl, cyclopropylmethyl, cyclobutylmethyl, or allyl; $R^1$ and $R^2$ are hydrogen; $R^3$ is {—}OH, {—}O-alkyl, {—)O-aryl, or {—}$OR^{1611}$; $R^5$, $R^{8a}$ $R^{8b}$, $R^9$, $R^{10a}$, $R^{10b}$, $R^{15a}$, $R^{15b}$, $R^{16a}$, and $R^{16b}$, if present, are hydrogen; $R^{14}$ is hydrogen, {—}OH, {—}O-alkyl, {—}$OR^{1611}$, or forms an alkano bridge with one of the $R^6$ pair, and $R^{18}$ is alkyl, halo-substituted alkyl, alkoxyalkyl, alkenyl, aryl, or substituted aryl. In one iteration, $R^{6a}$ is {—}OH, {—}O-alkyl, {—}$OR^{1611}$, or {—}$NR^{1611}R^{1612}$, and $R^{6b}$ is hydrogen, or together $R^{6a}$ and $R^{6b}$ form {=}O, {=}$CH_2$, or {—}$O(CH_2)_nO${—}, $R^{7a}$ and $R^{7b}$ are hydrogen, $R^{14}$ is hydrogen, {—}OH, {—}O-alkyl, or {—}$OR^{1611}$, and the dashed lines represent single bonds between the carbons at positions 6 and 7 and positions 8 and 14. In another iteration, $R^{6a}$ is {—}OH, {—}O-alkyl, or {—}$OR^{1611}$, $R^{6b}$ and $R^{14}$ form an alkano bridge, $R^{7a}$ is alkyl or substituted alkyl, $R^{7b}$ is hydrogen; and the dashed lines represent single bonds.

(a) Step A—Reaction Mixture

Step A of the process comprises contacting the compound comprising Formula (I) with a hydrocarbyl haloformate, $XC(O)OR^{18}$, and a proton acceptor to form the compound comprising Formula (II). The proton acceptor may be a hindered tertiary amine, an inorganic salt, or a combination thereof. The process commences with the formation of a reaction mixture comprising the compound comprising Formula (I), which is detailed above, the hydrocarbyl haloformate, and the proton acceptor.

(i) Hydrocarbyl Haloformate

A variety of hydrocarbyl haloformates are suitable for use in this process. In general, the hydrocarbyl haloformate is represented by the formula $XC(O)OR^{18}$, wherein X is halogen and $R^{18}$ is hydrocarbyl or substituted hydrocarbyl. In exemplary embodiments, X may be chloride or bromide, and $R^{18}$ may be alkyl, halo-substituted alkyl, alkoxyalkyl, alkenyl, aryl, or substituted aryl. Non-limiting examples of suitable hydrocarbyl haloformates include alkyl haloformates (such as, e.g., methyl chloroformate, methyl bromoformate, ethyl chloroformate, ethyl bromoformate, propyl chloroformate, propyl bromoformate, isopropyl chloroformate, isopropyl bromoformate, butyl chloroformate, butyl bromoformate, isobutyl chloroformate, isobutyl bromoformate, and the like); halo-substituted alkyl haloformates (such as, e.g., chloromethyl haloformate, bromomethyl haloformate, chloroethyl haloformate, bromoethyl haloformate, and so forth); alkenyl haloformates (such as, e.g., vinyl chloroformate, vinyl bromoformate, allyl chloroformate, allyl bromoformate, etc.), alkoxyalkyl haloformates (such as, e.g., methyoxymethyl chloroformate, methyoxymethyl bromoformate, ethoxymethyl chloroformate, ethoxymethyl bromoformate, and so forth); aryl haloformates (such as, benzyl chloroformate, benzyl bromoformate, phenyl chloroformate, phenyl bromoformate, menthyl chloroformate, menthyl bromoformate, nitrophenyl chloroformate, nitrophenyl bromoformate, and the like). In exemplary embodiments, the hydrocarbyl haloformate may be phenyl chloroformate, ethyl chloroformate, or chloroethyl chloroformate.

The amount of hydrocarbyl haloformate that is contacted with the compound comprising Formula (I) may vary. In general, the mole to mole ratio of the compound comprising Formula (I) to the hydrocarbyl haloformate may range from about 1:1 to about 1:4. In various embodiments, the mole to mole ratio of the compound comprising Formula (I) to the hydrocarbyl haloformate may be about 1:1.0, 1:1.1, 1:1.2, 1:1.3, 1:1.4, 1:1.5, 1:1.6, 1:1.7: 1:1.8, 1:1.9, 1:2.0, 1:2.1, 1:2.2, 1:2.3, 1:2.4, 1:2.5, 1:2.6, 1:2.7, 1:2.8, 1:2.9, 1:3.0, 1:3.2, 1:3.4, 1:3.6, 1:3.8, or 1:4.0. In exemplary embodiments, the mole to mole ratio of the compound comprising Formula (I) to the hydrocarbyl haloformate may range from about 1:1.5 to about 1:3.0.

(ii) Proton Acceptor is Hindered Amine and/or Inorganic Salt

The reaction mixture also comprises a proton acceptor. In general, the pKa of suitable proton acceptors ranges from about 7 to about 13. The proton acceptor may be organic or inorganic.

In some embodiments, the proton acceptor may be a sterically hindered tertiary amine. Non-limiting examples of suitable hindered tertiary amine include N,N-diisopropylethylamine, N,N-diisopropyl-2-ethylbutylamine; N,N-diisopropyl-3-pentylamine, triisopropylamine, triethylamine, N-ethylpiperidine, or combinations thereof.

In other embodiments, the proton acceptor may be an inorganic salt. The inorganic salt may be insoluble in the reaction mixture. Representative inorganic salts include, but are not limited to, borate salts (such as, for example, $Na_3BO_3$), di- and tri-basic phosphate salts (such as, for example, $Na_2HPO_4$ and $Na_3PO_4$), bicarbonate salts (such as, for example, $NaHCO_3$, $KHCO_3$, mixtures thereof, and the like), hydroxide salts (such as, for example, NaOH, KOH, mixtures thereof, and the like), carbonate salts (such as, for example, $Na_2CO_3$, $K_2CO_3$, mixtures thereof, and the like), and combinations of any of the foregoing. In still other embodiments, the proton acceptor may be a combination of a hindered tertiary amine and an inorganic salt, examples of which are detailed above.

The mole to mole ratio of the compound comprising Formula (I) to the proton acceptor may range from about 1:1 to about 1:6. In some embodiments, the mole to mole ratio of the compound comprising Formula (I) to the proton acceptor may be about 1:1.0, 1:1.5, 1:2.0, 1:2.4, 1:2.6, 1:2.8, 1:3.0, 1:3.2, 1:3.4, 1:3.6, 1:3.8, 1:4.0, 1:4.2, 1:4.4, 1:4.6, 1:4.8, 1:5.0, 1:5.5, or 1:6.0. In embodiments in which the proton acceptor is a hindered tertiary amine, the mole to mole ratio of the compound comprising Formula (I) to the hindered amine may range from about 1:1.6 to about 1:2.0. In embodiments in which the proton acceptor comprises an inorganic salt, the mole to mole ratio of the compound comprising Formula (I) to the proton acceptor may range from 1:2.5 to about 1:4.5. In embodiments in which the proton acceptor is a combination of a hindered amine and an inorganic salt, the mole to mole ratio of the hindered amine to the inorganic salt may range from about 1:7 to about 1:8.

(iii) Solvent

The reaction is generally conducted in the presence of a solvent or solvent system. The solvent may be a nonpolar organic solvent or a polar aprotic solvent. Representative nonpolar solvents include, but are not limited to, alkane and substituted alkane solvents (including cycloalkanes), aromatic hydrocarbons, esters, ethers, ketones, and combinations thereof. Specific nonpolar solvents that may be employed include, for example, benzene, butyl acetate, t-butyl methylether, t-butyl methyl ketone, chlorobenzene, chloroform, cyclohexane, dichloromethane, dichloroethane, diethyl ether, ethyl acetate, fluorobenzene, heptane, hexanes, methyl ethyl ketone (2-butanone), methyl isobutyl ketone, pentyl acetate, propyl acetates, toluene, and combinations thereof. Non-limiting examples of suitable aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl) ether, N,N-dimethylacetamide (DMA), N-methyl-2-pyrrolidinone (NMP), 1,4-dioxane, ethyl formate, formamide, hexamethylphosphoramide, methyl acetate, N-methylacetamide, N-methylformamide, methylene chloride, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof.

In embodiments in which the proton acceptor is a hindered amine, the solvent may be dichloromethane, dichloroethane, chloroform, acetonitrile, methyl ethyl ketone, methyl isobutylketone, toluene, or combinations thereof. In embodiments in which the proton acceptor comprises an inorganic salt, the solvent may be acetonitrile, chloroform, dichloroethane, methyl ethyl ketone, methyl isobutyl ketone, toluene, or combinations thereof.

In general, the volume to mass ratio of the solvent to the compound comprising Formula (I) ranges from about 0.5:1 to about 100:1. In various embodiments, the volume to mass ratio of the solvent to the compound comprising Formula (I) may range from 0.5:1 to about 5:1, from about 5:1 to about 25:1, or from about 25:1 to about 100:1. In exemplary embodiments, the volume to mass ratio of the solvent to the compound comprising Formula (I) may range from about 5:1 to about 20:1.

(b) Step A—Reaction Conditions

In general, the reaction is conducted at a temperature that ranges from about 0° C. to about 120° C. In various embodiments, the reaction may be conducted at a temperature from about 0° C. to about 20° C., from about 20° C. to about 40° C., from about 40° C. to about 60° C., from about 60° C. to about 80° C., from about 80° C. to about 100° C., or from about 100° C. to about 120° C. In embodiments in which the proton acceptor comprises a hindered amine, the reaction may be conducted at a temperature from about 20° C. to about 60° C. In embodiments in which the proton acceptor is an inorganic salt, the reaction may be conducted at a temperature from about 20° C. to about 80° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., HPLC) or another suitable method. In this context, a "completed reaction" generally means that the reaction mixture contains a significantly diminished amount of the compound comprising Formula (I), and a significantly increased amount of the compound comprising Formula (II) compared to the amounts of each present at the beginning of the reaction. Typically, the amount of the compound comprising Formula (I) remaining in the reaction mixture after the reaction is complete may be less than about 3%, or less than about 1%. In general, the reaction may proceed for about 20 minutes to about 24 hours. Typically, the duration of the reaction is longer at lower reaction temperatures. In certain embodiments, the reaction may be allowed to proceed for about a period of time ranging from about 0.5 hour to about 3 hours, from about 3 hours to about 5 hours, from about 5 hours to about 10 hours, or from about 10 hours to about 24 hours. In exemplary embodiments, the reaction may be allowed to proceed for about 2 hours to about 6 hours.

In some embodiments, the compound comprising Formula (II) may be isolated from the reaction mixture using techniques known to those of skill in the art. Non-limiting examples of suitable techniques include precipitation, extraction, evaporation, distillation, chromatography, and crystallization. In other embodiments, the compound comprising Formula (II) may not be isolated and step (b) of the process may proceed in the same reaction pot or reactor.

The yield of the compound comprising Formula (II) can and will vary. Typically, the yield of the compound comprising Formula (II) may be at least about 40%. In one embodiment, the yield of the compound comprising Formula (II) may range from about 40% to about 60%. In another embodiment, the yield of the compound comprising Formula (II) may range from about 60% to about 80%. In a further embodiment, the yield of the compound comprising Formula (II) may range from about 80% to about 90%. In still another embodiment, the yield of the compound comprising Formula (II) may be greater than about 90%, or greater than about 95%.

(c) Step B—Reaction Mixture

The process further comprises contacting the compound comprising Formula (II) with a hydrolysis agent such that the N-hydrocarboxycarbonyl group is removed from the compound comprising Formula (II) to form the compound comprising Formula (III). In some embodiments, the hydrolysis agent may be a quaternary ammonium salt. In other embodiments the hydrolysis agent may be a nucleophile and the reaction may be conducted in the presence of a solvent system comprising propylene glycol. In various iteration of this embodiment, the reaction may be conducted in the presence of a nucleophilic catalyst and/or a phase transfer reagent.

(i) Hydrolysis Agent is a Quaternary Ammonium Salt

In some embodiments, the hydrolysis agent may be a quaternary ammonium salt. A quaternary ammonium salt consists of a quaternary ammonium cation ($N^+R'R''R'''R''''$) and an anion. In general, R', R", R''', and R'''' of suitable quaternary ammonium cations are independently alkyl, substituted alkyl, aryl, or substituted aryl, wherein the alkyl generally has from one to six carbons atoms in the principle chain. Representative quaternary ammonium cations include, but are not limited to, tetramethylammonium, tetraethylammonium, tetrapropylammonium, tetra-n-butylammonium, tetrabenzylammonium, tetraphenylammonium, trimethylalkylammonium, trimethylalkylammonium, tripropylalkylammonium, tributylalkylammonium, and so forth. Non-limiting examples of suitable anions include bromide, chloride, fluoride, hydroxide, sulfonate, perchlorate, cyanide, and thiocynate. In exemplary embodiments, the quaternary ammonium salt may be tetra-n-butylammonium fluoride or tetra-n-butylammonium bromide.

The amount of quaternary ammonium salt added to the reaction mixture can and will vary. In general, the mole to mole ratio of the compound comprising Formula (II) to the quaternary ammonium salt may range from about 1:10 to about 1:100. In certain embodiments, the mole to mole ratio of the compound comprising Formula (II) to the quaternary ammonium salt may range from about 1:10 to about 1:20, from about 1:20 to about 1:40, from about 1:40 to about 1:80, or from about 1:80 to about 1:100. In certain embodiments, the mole to mole ratio of the compound comprising Formula (II) to the quaternary ammonium salt may range from about 1:20 to about 1:80. In one embodiment, the mole to mole ratio of the compound comprising Formula (II) to the quaternary ammonium salt may range from about 1:30 to about 1:40. In another embodiment, the mole to mole ratio of the compound comprising Formula (II) to the quaternary ammonium salt may range from about 1:70 to about 1:80.

Contact with the quaternary ammonium salt generally is conducted in the presence of a solvent or solvent system. Suitable solvents are detailed above in section (II)(a)(iii). In exemplary embodiments, the solvent may be dimethyl sulfoxide (DMSO), N,N-dimethylformamide (DMF), N,N-dimethylpropanamide (DMP), N,N-dimethylacetamide (DMA), N-methyl-2-pyrrolidinone (NMP), or combinations thereof.

In general, the volume to mass ratio of the solvent to the compound comprising Formula (II) ranges from about 0.5:1 to about 100:1. In various embodiments, the volume to mass ratio of the solvent to the compound comprising Formula (II) may range from 0.5:1 to about 5:1, from about 5:1 to about 25:1, or from about 25:1 to about 100:1. In exemplary embodiments, the volume to mass ratio of the solvent to the compound comprising Formula (II) may range from about 5:1 to about 20:1.

(ii) Hydrolysis Agent is a Nucleophile

In other embodiments, the hydrolysis agent may be a nucleophile. A variety of nucleophiles are suitable for use in this step of the process. In general, the nucleophile may have a pKa greater than about 13. Nucleophiles having this characteristic that are suitable for use in this process include hydroxides of alkali metals and alkaline earth metals (such as, for example, NaOH and $Ca(OH)_2$ and the like), and alkoxides (such as, e.g., methoxide, ethoxide, and so forth). In exemplary embodiments, the nucleophile may be alkali metal hydroxide, such as, e.g., potassium hydroxide or sodium hydroxide.

The amount of nucleophile added to the reaction mixture can and will vary. In general, the mole to mole ratio of the compound comprising Formula (II) to the nucleophile may range from about 1:2 to about 1:20. In various embodiments, the molar ratio of the compound comprising Formula (II) to the nucleophile may range from about 1:2 to about 1:4, from about 1:4 to about 1:6, from about 1:6 to about 1:8 from about 1:8 to about 1:10, from about 1:10 to about 1:15, or from about 1:15 to about 1:20. In one exemplary embodiment, the nucleophile is an alkali metal hydroxide and the mole to mole ratio of the compound comprising Formula (II) to the alkali metal hydroxide may range from about 1:5 to about 1:10.

Contact with the nucleophile may be performed in the presence of a solvent system comprising a glycol. Non-limiting examples of suitable glycols include propylene glycol (1,2-propanediol), diethylene glycol, methylene glycol, ethylene glycol, 1,3-propanediol, 1,2-butanediol, 1,3-butanediol, 1,4-butanediol, 2,3-butandiol, 1,5-pentanediol, 1,6-hexanediol, dipropylene glycol, triethylene glycol, tripropylamine glycol, or combinations thereof. In one embodiment, the solvent system comprises propylene glycol. In another embodiment, the solvent system consists of propylene glycol and water. In a further embodiment, the solvent system comprises diethylene glycol. In still other embodiments, the solvent system comprises a glycol, such as propylene glycol or diethylene glycol, in combination with one or more of acetonitrile, dioxane, propionitrile, pyridine, or water. In a further embodiment, the solvent system comprises a glycol, such as propylene glycol or diethylene glycol, in combination with one or more of the solvents listed above in section (II)(a)(iii). In alternate embodiments, the solvent system lacks a glycol and comprises one or more of the solvents listed above in section (II)(a)(iii). In one iteration, the solvent system lacks a glycol and comprises one or more of acetonitrile, dioxane, propionitrile, or pyridine.

In general, the volume to mass ratio of the solvent to the compound comprising Formula (II) ranges from about 0.5:1 to about 100:1. In various embodiments, the volume to mass ratio of the solvent to the compound comprising Formula (II) may range from 0.5:1 to about 5:1, from about 5:1 to about 25:1, or from about 25:1 to about 100:1. In exemplary embodiments, the volume to mass ratio of the solvent to the compound comprising Formula (II) may range from about 5:1 to about 20:1.

In embodiments in which the hydrolysis agent is a nucleophile, the reaction mixture may further comprise a nucleophilic catalyst, a phase transfer agent, or combinations thereof. Addition of the nucleophilic catalyst and/or the phase transfer agent may permit the reaction to proceed at a lower temperature, increase the reaction rate, increase yields and/or conversions, and/or reduce byproduct formation. Representative nucleophilic catalysts include, but are not limited to, imidazole, methylimidazole (NMI), pyridine, pyrrolidinopyridine (PPY), dimethylaminopyridine (DMAP), diazobicyclo[2.2.2]octane (DABCO), arginine, lysine, ornithine, or combinations thereof. Non-limiting examples of suitable phase transfer agents include quaternary ammonium salts such as, e.g., tetrabutylammonium salts, tetrahexylammonium salts, benzyltrimethylammonium salts, benzyltriethylammonium salts, methyltrioctylammonium salts, benzalkonium salts, and Aliquant 336; and quaternary phosphonium salts such as, e.g., tetramethylphosphonium salts, tetrabutylphosphonium salts, hexadecyltributylphosphonium salts, benzyltriphenylphosphonium salts, and dimethyldiphenylphosphonium salts. In general, the mole to mole ratio of the compound comprising Formula (II) to the nucleophilic catalyst or the phase transfer agent may range from about 1:0.0005 to about 1:0.5.

(d) Step B—Reaction Conditions

The temperature at which the reaction is conducted can and will vary. In general, the temperature of the reaction ranges from about 50° C. to about 140° C. In various embodiments, the temperature of the reaction may range from about 50° C. to about 70° C., from about 70° C. to about 90° C., from about 90° C. to about 110° C., from about 110° C. to about 125° C., or from about 125° C. to about 140° C. In embodiments in which the hydrolysis agent is a quaternary ammonium salt, the reaction may be conducted at a temperature that ranges from about 70° C. to about 100° C. In embodiments in which the hydrolysis agent is a nucleophile, the solvent comprises propylene glycol, and the reaction mixture lacks a nucleophilic catalyst or phase transfer agent, the temperature of the reaction may range from about 100° C. to about 130° C. However, in embodiments in which the hydrolysis agent is a nucleophile, the solvent system comprises acetonitrile, dioxane, propylene glycol, pyridine, water, or combinations thereof, and/or the reaction mixture contains one or more nucleophilic catalysts and/or phase transfer agents, the temperature of the reaction may range from about 60° C. to about 100° C.

Typically, the reaction is allowed to proceed for a sufficient period of time until the reaction is complete, as detailed above. In a completed reaction, the amount of the compound comprising Formula (II) remaining in the reaction mixture may be less than about 3%, or less than about 1%. In general, the reaction may proceed for about 1 hour to about 24 hours. In some embodiments, the reaction may proceed for about 1 hour to about 3 hours, from about 3 hours to about 4 hours, from about 4 hours to about 6 hours, from about 6 hours to about 8 hours, from about 8 hours to about 12 hours, from about 12 hours to about 18 hours, or from about 18 hours to about 24 hours.

The compound comprising Formula (III) may be isolated from the reaction mixture using techniques known to those of skill in the art. Non-limiting examples of suitable techniques include precipitation, extraction, evaporation, distillation, chromatography, and crystallization. The compound comprising Formula (III) may be used as is, or may be converted to another compound using techniques familiar to those of skill in the art.

The yield of the compound comprising Formula (III) can and will vary. Typically, the yield of the compound comprising Formula (III) may be at least about 35%. In one embodiment, the yield of the compound comprising Formula (III) may range from about 35% to about 65%. In another embodiment, the yield of the compound comprising Formula (III) may range from about 65% to about 75%. In yet another embodiment, the yield of the compound comprising Formula (III) may range from about 75% to about 85%. In a further embodiment, the yield of the compound comprising Formula (III) may range from about 85% to about 95%. In still another embodiment, the yield of the compound comprising Formula (III) may be greater than about 95%.

(e) Exemplary Embodiments

In certain embodiments, the process comprises contacting a compound comprising Formula (Ia) with a hydrocarbyl haloformate, $XC(O)OR^{18}$, and a proton acceptor to form a compound comprising Formula (IIa). The proton acceptor may be a hindered tertiary amine and/or an inorganic salt. The process further comprises contacting the compound comprising Formula (IIa) with a hydrolysis agent to form the compound comprising Formula (IIIa). The hydrolysis agent may be a quaternary ammonium salt or a nucleophile. Reaction Scheme 2 depicts the synthesis of the compound comprising Formula (IIIa) in accordance with this aspect of the disclosure:

Reaction Scheme 2:

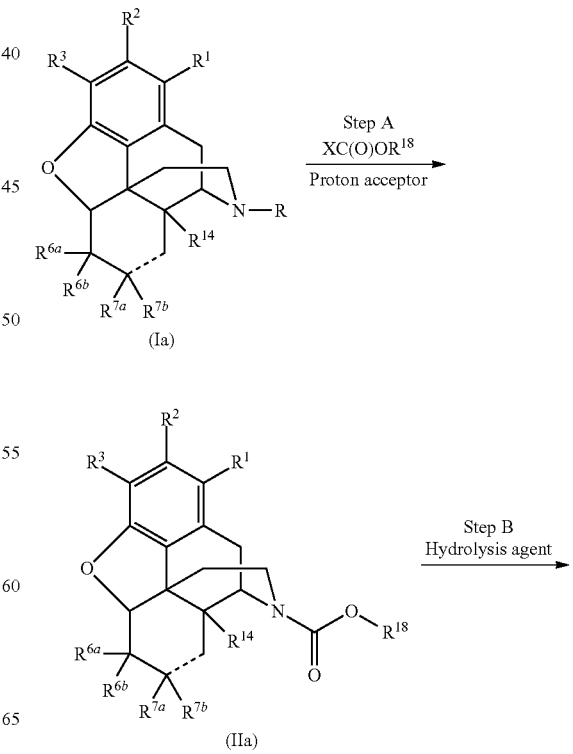

-continued

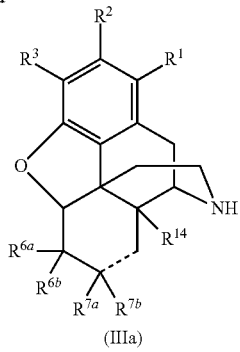

(IIIa)

wherein:

R is hydrocarbyl or substituted hydrocarbyl;

$R^1$, $R^2$, and $R^3$ are independently hydrogen, amino, halogen, {—}OH, {—}$OR^{1611}$, {—}SH, {—}$SR^{1611}$, {—}$NHR^{1611}$, {—}$NR^{1611}R^{1612}$, hydrocarbyl, or substituted hydrocarbyl;

$R^{6a}$ and $R^{6b}$ are independently hydrogen, amino, halogen, {—}OH, {—}$OR^{1611}$, {—}SH, {—}$SR^{1611}$, {—}$NHR^{1611}$, {—}$NR^{1611}R^{1612}$, hydrocarbyl, substituted hydrocarbyl, or together form a moiety chosen from {=}O, {=}S, {=}$CH_2$, {=}$NR^{1612}$; or {—}$O(CH_2)_nO${—}, wherein n is an integer of 1 or greater;

$R^{7a}$ and $R^{7b}$ are independently hydrogen, amino, halogen, {—}OH, {—}$OR^{1611}$, {—}SH, {—}$SR^{1611}$, {—}$NHR^{1611}$, {—}$NR^{1611}R^{1612}$, hydrocarbyl, or substituted hydrocarbyl;

$R^{14}$ is hydrogen, {—}OH, {—}O-alkyl, {—}$OR^{1611}$, or forms an alkano bridge with one of the $R^6$ pair;

$R^{18}$ is hydrocarbyl or substituted hydrocarbyl;

$R^{1611}$ and $R^{1612}$ are independently hydrocarbyl or substituted hydrocarbyl; and the dashed line is a single or double bond, provided only one of the $R^7$ pair is present when it is a double bond.

In exemplary embodiments, R is methyl, cyclopropylmethyl, cyclobutylmethyl, or allyl; $R^1$ and $R^2$ are hydrogen; $R^3$ is {—}OH, {—}O-alkyl, {—}O-aryl, or {—}$OR^{1611}$; and $R^{18}$ is alkyl, halo-substituted alkyl, alkoxyalkyl, alkenyl, aryl, or substituted aryl. In one iteration, $R^{6a}$ is {—}OH, {—}O-alkyl, {—}$OR^{1611}$, or {—}$NR^{1611}R^{1612}$, and $R^{6b}$ is hydrogen, or together $R^{6a}$ and $R^{6b}$ form {=}O, {=}$CH_2$, or {—}$O(CH_2)_nO${—}, $R^{7a}$ and $R^{7b}$ are hydrogen, $R^{14}$ is hydrogen, {—}OH, {—}O-alkyl, or {—}$OR^{1611}$, and the dashed lines represent a single bond. In another iteration, $R^{6a}$ is {—}OH, {—}O-alkyl, or {—}$OR^{1611}$, $R^{6b}$ and $R^{14}$ form an alkano bridge, $R^{7a}$ is alkyl or substituted alkyl, $R^{7b}$ is hydrogen; and the dashed lines represent a single bond.

The steps of the process are detailed above in sections (II)(a)-(d).

(f) Downstream Applications

In some embodiments, the compound comprising Formula (III) or (IIIa) may be converted into a pharmaceutically acceptable salt. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds comprising Formula (III) or (IIIa) may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with the any compound comprising Formula (III) or (IIIa).

In other embodiments, the compound comprising Formula (III) or (IIIa) may be converted into a "nal" compound, such as, e.g., naloxone, naltrexone, nalbuphene, nalmefene, or nalfurafine, by contact with a suitable N-alkylating agent. In still other embodiments, the compound comprising Formula (III) or (IIIa) may be derivatized to form a compound such as buprenorphine, etorphine, dihydroetorphine, diprenorphine, and the like.

(g) Stereochemistry

The compound comprising any of Formulas (I), (Ia), (II), (IIa), (III), or (IIIa) may have a (−) or a (+) orientation with respect to the rotation of polarized light. More specifically, each chiral center of the morphinans or normorphinans may have an R or an S configuration. The compounds described herein may have at least four chiral centers, namely carbons C-5, C-9, C-13, and C-14. At each chiral center, the stereochemistry at the carbon atom is independently R or S. The configuration of C-5, C-9, C-13, and C-14, respectively, may be RRRR, RRRS, RRSR, RSRR, SRRR, RRSS, RSSR, SSRR, SRRS, SRSR, RSRS, RSSS, SRSS, SSRS, SSSR, or SSSS, provided that the C-15 and C-16 atoms are both on the alpha face of the molecule or both on the beta face of the molecule.

(III) Process for the Preparation of a Compound Comprising Formula (III) from a Compound Comprising Formula (II)

In an additional aspect, the disclosure provides a process for the preparation of a compound comprising Formula (III) from a compound comprising Formula (II). The process comprises contacting the compound comprising Formula (II) with a quaternary ammonium salt to form the compound comprising Formula (III) as depicted in Reaction Scheme 3:

Reaction Scheme 3:

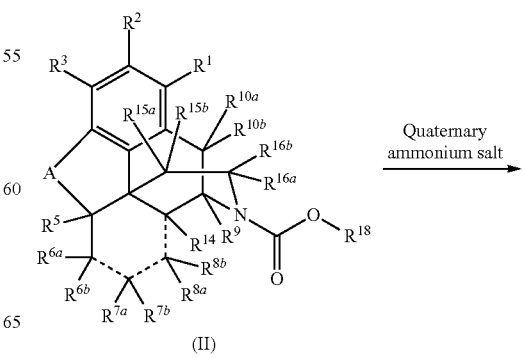

(II)

-continued

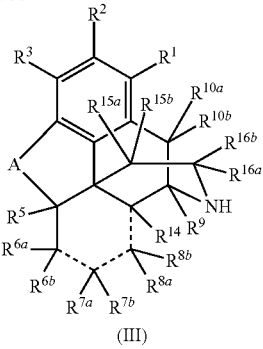

(III)

wherein:

A is oxygen, sulfur, or nitrogen;

$R^1$, $R^2$, and $R^3$ are independently hydrogen, amino, halogen, {—}OH, {—}$OR^{1611}$, {—}SH, {—}$SR^{1611}$, {—}$NHR^{1611}$, {—}$NR^{1611}R^{1612}$, hydrocarbyl, or substituted hydrocarbyl;

$R^5$, $R^{6a}$, $R^{6b}$, $R^{7a}$, $R^{7b}$, $R^{8a}$ $R^{8b}$, $R^9$, $R^{10a}$, $R^{10b}$, $R^{14}$, $R^{15a}$, $R^{15b}$, $R^{16a}$, and $R^{16b}$ are independently hydrogen, amino, halogen, {—}OH, {—}$OR^{1611}$, {—}SH, {—}$SR^{1611}$, {—}$NHR^{1611}$, {—}$NR^{1611}R^{1612}$, hydrocarbyl, or substituted hydrocarbyl; wherein any pair of $R^{\#a}$ and $R^{\#b}$ wherein # is any one of 6, 7, 8, 10, 15, 16, optionally together form a moiety chosen from {=}O, {=}S, {=}$CH_2$, {=}$NR^{1612}$, or {—}$O(CH_2)_nO${—}, wherein n is an integer of 1 or greater;

$R^{18}$ is hydrocarbyl or substituted hydrocarbyl $R^{1611}$ and $R^{1612}$ are independently hydrocarbyl or substituted hydrocarbyl;

one or more of $R^1$, $R^2$, $R^3$, $R^5$, $R^{6a}$, $R^{6b}$, $R^{7a}$, $R^{7b}$, $R^{8a}$ $R^{8b}$, $R^9$, $R^{10a}$, $R^{10b}$, $R^{14}$, $R^{15a}$, $R^{15b}$, $R^{16a}$, and $R^{16b}$ optionally forms part of a ring or ring system chosen from carbocyclic, substituted carbocyclic, heterocyclic, substituted heterocylic, or a combination thereof; and the dashed lines between the carbon atoms at positions 6 and 7, 7 and 8, and 8 and 14 represent carbon to carbon bonds chosen from (a) single bonds between all carbon atoms, wherein optionally one of the $R^6$ pair and $R^{14}$ form an alkano bridge; (b) single bonds between the carbons at both positions 7 and 8 and 8 and 14, and a double bond between the carbons at positions 6 and 7, wherein only one of $R^6$ pair is present; (c) single bonds between the carbons at both positions 6 and 7 and 8 and 14, and a double bond between the carbons at positions 7 and 8, wherein only one of each $R^7$ and $R^8$ pair is present; or (d) double bonds between the carbons at both positions 6 and 7 and 8 and 14, and a single bond between the carbons at positions 7 and 8, wherein only one of each $R^6$, $R^7$, and $R^8$ pair is present and $R^{14}$ is not present.

In one embodiment, A is oxygen. In another embodiment, $R^1$, $R^2$, $R^3$, $R^5$, $R^{6a}$, $R^{6b}$, $R^{7a}$, $R^{7b}$, $R^{8a}$ $R^{8b}$, $R^9$, $R^{10a}$, $R^{10b}$, $R^{14}$, $R^{15a}$, $R^{15b}$, $R^{16a}$, and $R^{16b}$, if present, are independently hydrogen, halogen, hydroxyl, alkoxy, acyl, alkyl, alkenyl, aryl, substituted alkyl, substituted alkenyl, or substituted aryl. In a further embodiment, R and $R^{18}$ are independently alkyl, alkenyl, alkynyl, aryl, substituted alkyl, substituted alkenyl, substituted alkynyl, or substituted aryl.

In exemplary embodiments, A is oxygen, R is methyl, ethyl, cyclopropylmethyl, cyclobutylmethyl, or allyl; $R^1$ and $R^2$ are hydrogen; $R^3$ is {—}OH, {—}O-alkyl, {—)O-aryl, or {—}$OR^{1611}$; $R^5$, $R^{8a}$ $R^{8b}$, $R^9$, $R^{10a}$, $R^{10b}$, $R^{15a}$, $R^{15b}$, $R^{16a}$, and $R^{16b}$, if present, are hydrogen; $R^{14}$ is hydrogen, {—}OH, {—}O-alkyl, {—}$OR^{1611}$, or forms an alkano bridge with one of the $R^6$ pair, and $R^{18}$ is alkyl, halo-substituted alkyl, alkoxyalkyl, alkenyl, aryl, or substituted aryl. In one iteration, $R^{6a}$ is {—}OH, {—}O-alkyl, {—}$OR^{1611}$, or {—}$NR^{1611}R^{1612}$, and $R^{6b}$ is hydrogen, or together $R^{6a}$ and $R^{6b}$ form {=}O, {=}$CH_2$, or {—}$O(CH_2)_nO${—}, $R^{7a}$ and $R^{7b}$ are hydrogen, $R^{14}$ is hydrogen, {—}OH, {—}O-alkyl, or {—}$OR^{1611}$, and the dashed lines represent single bonds between the carbons at positions 6 and 7 and positions 8 and 14. In another iteration, $R^{6a}$ is {—}OH, {—}O-alkyl, or {—}$OR^{1611}$, $R^{6b}$ and $R^{14}$ form an alkano bridge, $R^{7a}$ is alkyl or substituted alkyl, $R^{7b}$ is hydrogen; and the dashed lines represent single bonds.

(a) Reaction Mixture

The process commences with the formation of a reaction mixture comprising the compound comprising Formula (II) and a quaternary ammonium salt. A quaternary ammonium salt consists of a quaternary ammonium cation ($N^+R'R''R'''R''''$) and an anion. In general, R', R'', R''', and R'''' of suitable quaternary ammonium cations are independently alkyl, substituted alkyl, aryl, or substituted aryl, wherein the alkyl generally has from one to six carbons atoms in the principle chain. Representative quaternary ammonium cations include, but are not limited to, tetramethylammonium, tetraethylammonium, tetrapropylammonium, tetra-n-butylammonium, tetrabenzylammonium, tetraphenylammonium, trimethylalkylammonium, triethylalkylammonium, tripropylalkylammonium, tributylalkylammonium, and so forth. Non-limiting examples of suitable anions include bromide, chloride, fluoride, hydroxide, sulfonate, perchlorate, cyanide, and thiocynate. In exemplary embodiments, the quaternary ammonium salt may be tetra-n-butylammonium fluoride or tetra-n-butylammonium bromide.

The amount of quaternary ammonium salt added to the reaction mixture can and will vary. In general, the mole to mole ratio of the compound comprising Formula (II) to the quaternary ammonium salt may range from about 1:10 to about 1:100. In certain embodiments, the mole to mole ratio of the compound comprising Formula (II) to the quaternary ammonium salt may range from about 1:10 to about 1:20, from about 1:20 to about 1:40, from about 1:40 to about 1:80, or from about 1:80 to about 1:100. In certain embodiments, the mole to mole ratio of the compound comprising Formula (II) to the quaternary ammonium salt may range from about 1:20 to about 1:80. In one embodiment, the mole to mole ratio of the compound comprising Formula (II) to the quaternary ammonium salt may range from about 1:30 to about 1:40. In another embodiment, the mole to mole ratio of the compound comprising Formula (II) to the quaternary ammonium salt may range from about 1:70 to about 1:80.

Contact with the quaternary ammonium salt generally is conducted in the presence of a solvent. Suitable solvents are detailed above in section (II)(a)(iii). In exemplary embodiments, the solvent may be dimethyl sulfoxide (DMSO), N,N-dimethylformamide (DMF), N,N-dimethylpropanamide (DMP), N,N-dimethylacetamide (DMA), N-methyl-2-pyrrolidinone (NMP), or combinations thereof.

In general, the volume to mass ratio of the solvent to the compound comprising Formula (II) ranges from about 0.5:1 to about 100:1. In various embodiments, the volume to mass ratio of the solvent to the compound comprising Formula (II) may range from 0.5:1 to about 5:1, from about 5:1 to about 25:1, or from about 25:1 to about 100:1. In exemplary embodiments, the volume to mass ratio of the solvent to the compound comprising Formula (II) may range from about 5:1 to about 20:1.

(b) Reaction Conditions

The temperature at which the reaction is conducted can and will vary. In general, the temperature of the reaction ranges from about 50° C. to about 140° C. In various embodiments, the temperature of the reaction may range from about 50° C. to about 70° C., from about 70° C. to about 90° C., from about 90° C. to about 110° C., from about 110° C. to about 125° C., or from about 125° C. to about 140° C. In exemplary embodiments, the reaction may be conducted at a temperature that ranges from about 70° C. to about 100° C.

Typically, the reaction is allowed to proceed for a sufficient period of time until the reaction is complete, as detailed above. In a completed reaction, the amount of the compound comprising Formula (II) remaining in the reaction mixture may be less than about 3%, or less than about 1%. In general, the reaction may proceed for about 1 hour to about 12 hours. In various embodiments, the reaction may proceed for about 1 hour to about 3 hours, from about 3 hours to about 4 hours, from about 4 hours to about 6 hours, from about 6 hours to about 8 hours, or from about 8 hours to about 12 hours.

The compound comprising Formula (III) may be isolated from the reaction mixture using techniques known to those of skill in the art. The yield of the compound comprising Formula (III) is detailed above in section (II)(d), and the stereochemistry of the compound is described above in section (II)(g). The compound comprising Formula (III) may be converted to a pharmaceutically acceptable salt or converted into another compound as detailed above in section (II)(f).

DEFINITIONS

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "oxygen protecting group" as used herein denotes a group capable of protecting an oxygen atom (and hence, forming a protected hydroxyl group), wherein the protecting group may be removed, subsequent to the reaction for which protection is employed, without disturbing the remainder of the molecule. Exemplary oxygen protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of oxygen protecting groups and the synthesis thereof may be found in "Greene's Protective Groups in Organic Synthesis," 4$^{th}$ Ed. by P. G. M. Wuts and T. W. Greene, John Wiley & Sons, Inc., 2007.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate certain embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Examples 1-5

Synthesis of N-Phenoxycarbonyl Nordihydrothebaine

Examples 1-5 detail the synthesis of (+)-N-phenoxycarbonyl nordihydrothebaine from (+)-dihydrothebaine in which a variety of solvents and reaction conditions were tested. The reaction was as follows:

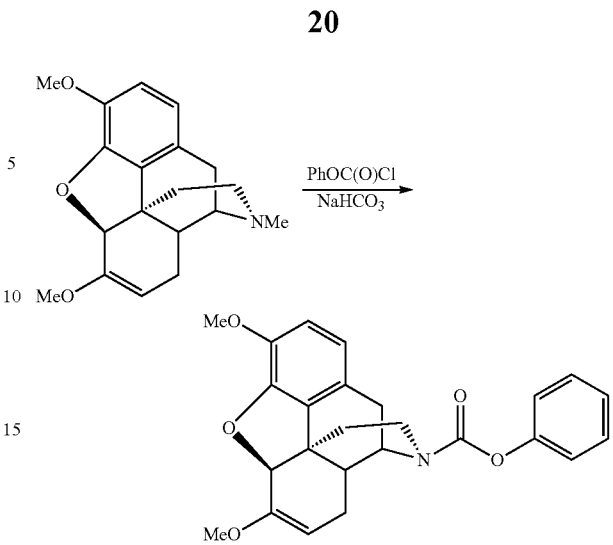

Example 1

To a dried three neck reaction flask was charged 30 g (+)-dihydrothebaine, 33 g sodium bicarbonate, and 210 mL of dichloroethane. Next, 24 mL phenyl chloroformate was added and the resulting mixture was heated to 75° C. under nitrogen. After stirring at 75° C. for 45 minutes, the reaction was cooled to room temperature. The solid was filtered and the filtrate was diluted by adding 105 mL dichloromethane. To the resulting solution was added 240 mL of 0.52 N NaOH aqueous solutions. After stirring at room temperature for 2 hours, the aqueous phase was separated and disregarded. The organic phase was further washed with 240 mL 0.52 N sodium hydroxide solution three times and once with 240 mL water, and then dried over anhydrous magnesium sulfate. After filtration and removal of volatiles, the residue was re-crystallized from a mixture of isopropanol/dichloromethane to yield 33.2 g of light yellow carbamate derivative solid.

Example 2

A series of reactions was performed in which a variety of different solvents, reaction temperatures, and reaction time were tested. The various reaction conditions are listed in Table 1. In general, to a dried three neck reaction flask was charged 1 g of (+)-dihydrothebaine, 1.1 g sodium bicarbonate, 0.8 mL phenyl chloroformate, and 7 mL solvent; the resulting mixture was stirred under nitrogen at the desired temperature for the desired period of time. After cooling to room temperature, the reaction was quenched by adding 10 mL water and 7 mL dichloromethane. After stirring for 15 min, the organic phase was separated and treated with 8 mL 0.52 N NaOH aqueous solution for 2 hours, and then the organic phase was separated and further washed with 7 mL 0.52 N sodium hydroxide three times. The organic phase was then washed with 7 mL of 5% formic acid once, 8 mL of water once, and then dried over magnesium sulfate. After filtration and removal of volatiles, the crude material was re-crystallized from isopropanol to yield desired carbamate derivative (see Table 1). It was found that reaction in the presence of dichlorethane resulted in high yields even at low temperatures.

TABLE 1

Conditions and Yield

| Reaction | Solvent | Temperature (°C.) | Reaction Time | Carbamate Derivative (g) |
|---|---|---|---|---|
| 2a | Dichloroethane | 20° C. | 20 hrs | 0.76 g |
| 2b | Dichloroethane | 50° C. | 3 hrs | 1.0 g |
| 2c | Dichloroethane | 65° C. | 1.5 hrs | 0.95 g |
| 2d | Dichloroethane | 80° C. | 45 min | 0.98 g |
| 2e | Toluene | 80° C. | 2.5 hrs | 0.87 g |
| 2f | Methyl ethyl ketone (2-Butanone) | 50° C. | 7 hrs | 0.57 g |
| 2g | Methyl isobutyl ketone | 50° C. | 4 hrs | 0.71 g |

Example 3

To a dried three neck reaction flask was charged 98 g of (+)-dihydrothebaine, 84 g sodium bicarbonate, and 708 mL acetonitrile. The resulting mixture was stirred under nitrogen in ice bath for 10 minutes, and to the reaction was charged 64.5 mL phenyl chloroformate. The resulting reaction was heated to 50° C. for three hours. After the reaction was cooled to room temperature, to the reaction was added 708 mL ethyl acetate and 300 mL water. To the separated organic phase was charged another 300 mL of ethyl acetate and 100 mL dichloromethane. The resulting organic phase was washed with 0.5 N NaOH solutions four times, brine once, and then dried over anhydrous magnesium sulfate. After filtration and removal of volatiles, the residue was re-crystallized from a mixture of isopropanol and chloroform to yield 112 g carbamate derivative.

Example 4

To a dried three neck reaction flask was charged 35.5 g of (+)-dihydrothebaine, 39 g sodium bicarbonate, 12.4 g anhydrous magnesium sulfate, and 256 mL acetonitrile. The resulting mixture was stirred under nitrogen for 30 minutes and then cooled in ice bath for 15 minutes. To the reaction was charged 28.4 mL of phenyl chloroformate. The resulting reaction was heated to 50° for three hours. After the reaction was cooled to room temperature, the mixture was filtered and washed with dichloromethane. The combined filtrate and washings were treated with 0.52 N NaOH aqueous solution for two hrs. The organic phase was separated and further washed with 300 mL of 0.52 N NaOH aqueous solution three times, 0.3% HCl once, 10% brine once, and then dried over anhydrous magnesium sulfate. After filtration and removal of volatiles, the crude material was crystallized from isopropanol/ethyl acetate to yield 38.2 g carbamate derivative.

Example 5

To a dried three neck reaction flask was charged 15.1 g of (+)-dihydrothebaine, 13 g sodium bicarbonate, and 113 mL chloroform. After stirring under nitrogen in ice bath for 10 minutes, to the reaction mixture was added 10 mL phenyl chloroformate. The reaction was heated to 50° for five hours. Then to the reaction was added another 8.3 g sodium bicarbonate and 6.6 mL phenyl chloroformate. The reaction continued at 50° for another two hours. After cooling to room temperature, to the reaction was added 300 mL dichloromethane. The solid was filtered out, the organic filtrate was washed with 120 mL of 1.0 N sodium hydroxide aqueous solution three times, 4% formic acid three times, water once, then dried over anhydrous magnesium sulfate. After filtration and removal of volatiles, the crude material was crystallized in IPA to yield 17.4 g carbamate derivative.

Example 6

Synthesis of N-Ethoxycarbonyl Nordihydrothebaine

N-ethoxycarbonyl nordihydrothebaine was prepared from dihydrothebaine according to the following reaction scheme:

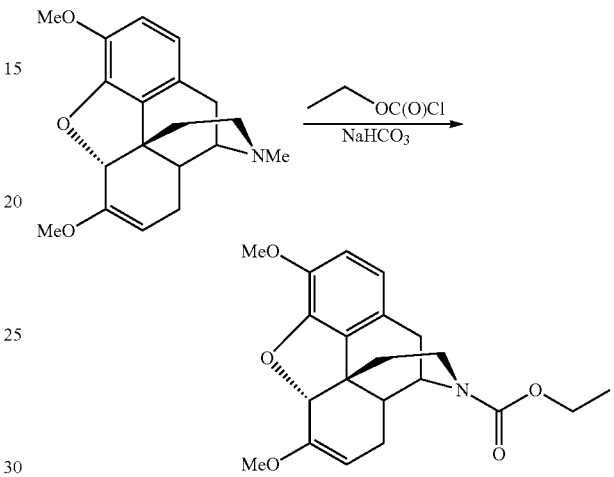

To a mixture of 25.03 g of the (−)-dihydrothebaine, 28.08 g of NaHCO$_3$ and 175 mL of ethanol-free chloroform was added 23 mL of ethyl chloroformate. This took the reaction mixture from room temperature to 33° C. The mixture was kept at over 50° C. for 4.5 hours and then stirred at room temperature overnight. The mixture was cooled in ice and quenched slowly with 300 mL of water. The mixture was poured into a separatory funnel and the flask washed with 100 mL of water, which was added to the funnel. The layers were separated. The water layer was extracted with 200 mL of chloroform. The combined chloroform phase was stirred with 25 g of MgSO$_4$ for half an hour. After filtration and removal of the volatiles, it yielded 35 g oil carbamate derivative with 98% area purity.

Example 7

Synthesis of Phenylcarbamate Derivative in the Presence of a Hindered Amine

Dihydrothebaine was demethylated by phenyl chloroformate in the presence of N,N-diisopropylethylamine (DIPEA) and/or NaHCO$_3$ according to the following reaction scheme:

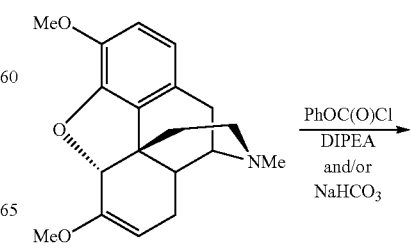

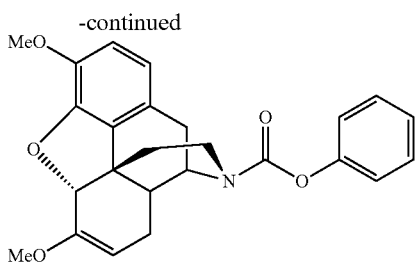

For the reaction, (−)-dihydrothebaine (DHT) was reacted with 2.5 equivalents of phenyl chloroformate in a 10:1 volume to mass ratio of dichloromethane to substrate. The amounts of DIPEA and/or NaHCO₃ added to each reaction are presented in Table 2. The reaction was allowed to proceed for 2 hours at 40° C. Table 2 presents the yield of the carbamate. The presence of the hindered amine resulted in a higher conversion of the substrate to the demethylated compound.

TABLE 2

Conditions and Yield.

| Reaction | DIPEA (Eq) | NaHCO₃ (Eq) | Carbamate (HPLC % area) | DHT (HPLC % area) |
|---|---|---|---|---|
| 7a | 1.8 | — | 91.7 | 0.3 |
| 7b | 0.4 | 3 | 87.1 | 0.7 |
| 7c | — | 3 | 72.9 | 13.9 |

Example 8

Synthesis of Chloroethyl Carbamate Derivative in the Presence of a Hindered Amine Dihydrothebaine was demethylated by chloroethyl chloroformate in the presence of N,N-diisopropylethylamine (DIPEA) and/or NaHCO₃ according to the following reaction scheme:

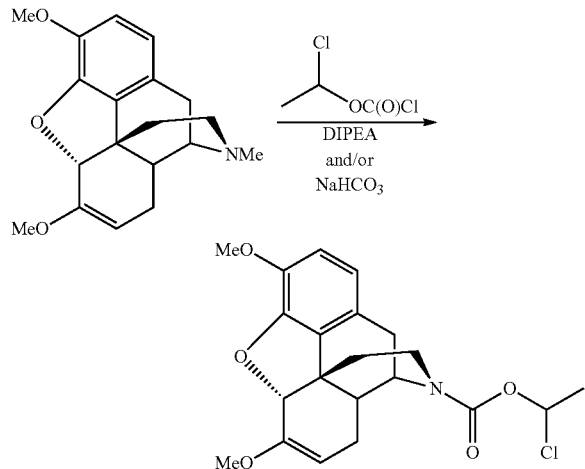

(−)-Dihydrothebaine (DHT) was reacted with 2.5 equivalents of 1-chlorotheyl chloroformate in a 10:1 volume to mass ratio of methanol to substrate. The amounts of DIPEA and/or NaHCO₃ added to each reaction are presented in Table 3. The reaction was allowed to proceed for 2 hours at 40° C. Table 3 presents the yield of the carbamate. The presence of the hindered amine resulted in a higher conversion of the substrate to the demethylated compound.

TABLE 3

Conditions and Yield

| Reaction | DIPEA (Eq) | NaHCO₃ (Eq) | Carbamate (HPLC % area) | DHT (HPLC % area) |
|---|---|---|---|---|
| 8a | 1.8 | — | 93.3 | 0.5 |
| 8b | 0.4 | 3 | 94.4.1 | 0.3 |
| 8c | — | 4 | 80.0.9 | 16.3 |

Example 9

Hydrolysis of N-Phenoxycarbonyl Nordihydrothebaine

N-phenoxycarbonyl dihydrothebaine was hydrolyzed to nordihydrothebaine according to the following reaction scheme:

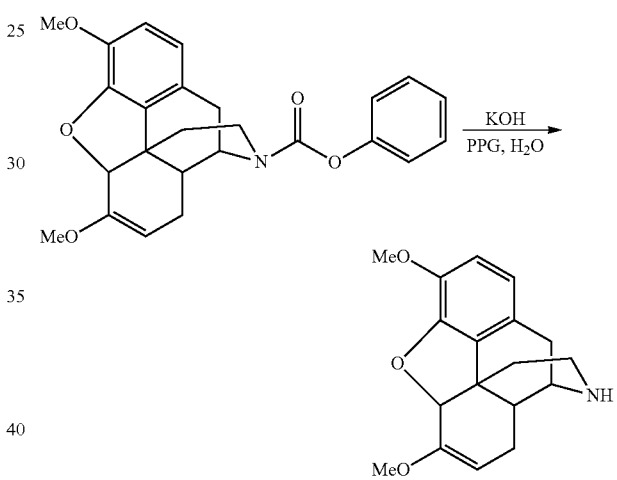

A mixture of KOH, nordihydrothebaine phenylcarbamate, propylene glycol (PPG; which was used to wash in the opiate off the funnel), and water was placed into a half liter Hastelloy Parr reactor, flushed with nitrogen and closed. Table 4 presents the amounts of substrate, KOH, PPG, and water used in four separate experiments. The reactor was heated for four hours over 100° C., with at least three hours at 115-125° C. After cooling to room temperature, to the reactor was added 7.8 mL of water per gram of starting carbamate; the mixture was stirred and poured into a beaker. The internal parts of the reactor were rinsed with a minimal amount of water, which was added to the water mixture in the beaker. The mixture was stirred in an ice bath with 9.4 mL of dichloromethane per gram of carbamate. The layers were separated. The aqueous layer was extracted four times with 6.2 mL of dichloromethane per gram of carbamate each time. The organic extracts were combined. After removal of the volatiles in the combined organic extracts, an oil residue remained. The oil residue was dissolved in 9.4 mL of dichloromethane per gram of carbamate and then washed with 2M NaOH; the dichloromethane was removed, and to the residue was added 0.94 mL of methanol per gram of carbamate. After removal of all volatiles, the residue oil was re-dissolved in 3.75 mL of ethyl acetate per gram starting carbamate. The mixture was stirred and allowed to cool. The resulting solid was harvested by filtration, washed with ethyl acetate, and dried under vacuum to give solid product. The amount of nordihydrothebaine yielded is presented in Table 4.

TABLE 4

Reactants and Yield

| Reaction | Phenylcarbamate Substrate* | KOH | PPG | Water | Product yielded |
|---|---|---|---|---|---|
| 9a | 32 g | 27 g | 205 mL | 64 mL | 16.3 g |
| 9b | 150 g | 135 g | 850 mL | 320 mL | 87.2 g |
| 9c | 25.0 g | 22.5 g | 140 mL | 53 mL | 15.1 g |
| 9d | 20.85 g | 18.9 g | 81 mL | 81 mL | 14.1 g |

*Reaction 9b used (+)-nor-dihydrothebaine phenylcarbamate; the other reactions used (−)-nor-dihydrothebaine phenylcarbamate.

Example 10

Hydrolysis of N-Ethoxycarbonyl Nordihydrothebaine

Nordihydrothebaine ethyl carbamate was hydrolyzed to nordihydrothebaine according to the following reaction scheme:

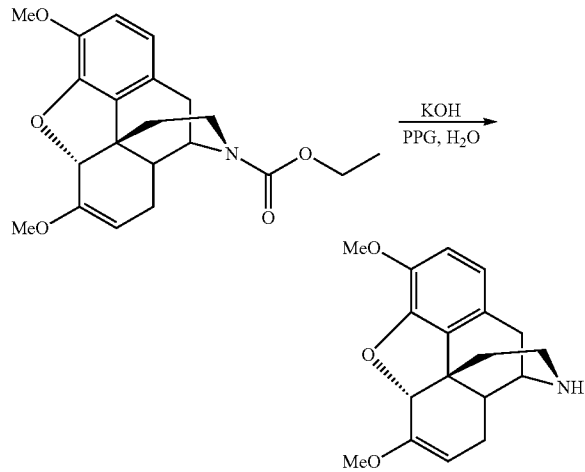

Thirty five g of crude (−)-17-ethylcarbomatyl-4,5-epoxy-3-methoxy-6-methoxy-(5α)-morphinan-6-ene (assumed to contain 29-30 g of the desired material plus residual solvent plus 6 g of additional solid material) was stirred into 40 mL of isopropanol. The compound started to crystallize, so the mixture was heated enough to dissolve the compound. The warm mixture was poured into a half liter Parr reactor and the starting container rinsed with 20 mL of isopropanol, which was added to the reactor. To the reactor was added 220 mL of propylene glycol, 80 mL of water and 35 g of KOH. The reactor was flushed with nitrogen and closed. The reaction was heated for a total of 12 hours at over 120° C. (with a total range of 110-125° C.) before sampling the first time. By HPLC area, 90% was nordihydrothebaine with 1.7% of the carbamate left. Heating for an additional 2 hours above 110° C. resulted in 0.8% of the carbamate remaining. The contents were washed out of the reactor with 200 mL water and stirred with 300 mL of dichloromethane. The water layer was extracted twice with 150 mL dichloromethane. The dichloromethane extractions were combined and washed with 100 mL of water. Rotary evaporating gave 36 g of oil. Heating this in 125 mL of ethyl acetate gave solid. The contents were rota-evaporated to 89 g. Cooling in an ice bath followed by filtration gave 16.2 g nordihydrothebaine (58%).

Example 11

Synthesis of Nordihydrothebaine HCl Salt

A sample (12.9 g) of the crude oil (−)-nordihydrothebaine prepared in Example 10, without crystallizing, was dissolved in 50 mL isopropanol by heating. To the warm mixture was added 4.4 g of concentrated hydrochloric acid. Solid was allowed to precipitate. The mixture was filtered at room temperature and washed with cold isopropanol. Oven drying gave 13.0 g (−)-nordihydrothebaine hydrochloride salt.

Example 12

Modifications of the Hydrolysis Reaction

Several different solvent systems were tested to determine whether the hydrolysis reaction could be performed at lower temperatures. A decrease in reaction temperature can decrease the caustic corrosion of glass. Phase transfer agents were included if the starting carbamate was not completely soluble at lower temperatures. Additionally, nucleophilic catalysts were tested to determine whether they would increase the rate of hydrolysis.

In one experiment, (+)-nordihydrothebaine phenylcarbamate was better dissolved at 80° C. with a mixture of propionitrile and propylene glycol, along with aqueous potassium hydroxide, than with propylene glycol and aqueous potassium hydroxide (as used in Example 9). The rate of hydrolysis was initially faster at 80° C. in the propionitrile and propylene glycol solvent system as compared with the standard solvent system. As the reaction proceeded, however, the propionitrile began to hydrolyze, which consumed the potassium hydroxide and decreased the carbamate hydrolysis rate. It is anticipated that this process can be modified by metering the addition of the potassium hydroxide into the reaction mixture in order to maintain a consistently fast hydrolysis rate.

In another experiment, sub-stoichiometric amounts of arginine were added to the standard propylene glycol solvent mixture and the reaction was heated at the standard 110° C. The nordihydrothebaine phenylcarbamate was observed to fully hydrolyze to nordihydrothebaine within one hour, 45 minutes as compared with 3 hours for the uncatalyzed reaction at the same solvent and temperature conditions.

Additionally, a solvent system comprising dioxane and water was used. Because the reaction mixture was not completely miscible at 80° C., the reaction exhibited a slow hydrolysis rate at this temperature. Tetrabutylammonium bromide was then added as a phase transfer agent. The hydrolysis rate at 80° C. was observed to dramatically increase. Further, a reaction mixture, which contained sub-stoichiometric amounts of imidazole, exhibited a hydrolysis rate which was twice as fast as the rate for an uncatalyzed reaction mixture. In another experiment, a mixture of dioxane and propylene glycol was observed to form a single phase with water, potassium hydroxide, and the substrate at 80° C.

In still another experiment, a mixture of dioxane and pyridine was combined with aqueous potassium hydroxide and the substrate. At 80° C., a reaction mixture containing sub-stoichiometric amounts of imidazole was observed to hydrolyze 2.6 times faster than an uncatalyzed reaction. At 80° C., a reaction mixture containing tetrabutylammonium bromide was observed to hydrolyze 1.6 times faster than an uncatalyzed reaction. Because the imidazole is a nucleophilic catalyst and the tetrabutylammonium bromide is a phase transfer agent, the two substances should be accelerating the reaction by two different mechanisms. Therefore, it is expected that a combination of these two substances would be additive, or even synergistic.

Example 13

Hydrolysis With Tetrabutyl Ammonium Salt

Cyclic-ethyleneacetal-N-phenoxycarbonyl nordihydrocodeinone was hydrolyzed under mild conditions into cyclic-ethyleneacetal-nordihydrocodeinone according to the following reaction:

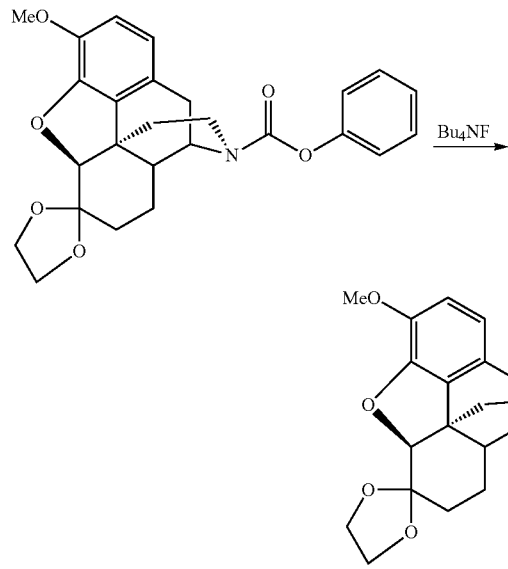

(+)-Cyclic-ethyleneacetal-N-phenoxycarbonyl nordihydrocodeinone was mixed with a solvent in 10:1 volume to mass ratio of solvent to substrate. To this was added a volume of 1.0 M tetrabutylammonium fluoride in THF. Table 5 lists the solvent and amount of tetrabutylammonium fluoride used in each reaction. The resulting mixture was heated in an oil bath to a first temperature as the THF was distilled off. Then the reaction mixture was kept at a second temperature under nitrogen for certain period of time. The temperatures and times are listed in Table 5. The product was analyzed by HPLC and the yield (i.e., integration area of the product) for each reaction is shown in Table 5. High yields of nordihydrocodeinone were obtained under the mild hydrolysis conditions.

TABLE 5

| | | Reaction Conditions and Yield | | | | |
|---|---|---|---|---|---|---|
| Reaction | Solvent | Bu$_4$NF (ml/g of substrate) | 1$^{st}$ Temp (° C.) | 2$^{nd}$ Temp (° C.) | Time | Product Yield |
| 13a | Dimethyl sulfoxide | 22 | 106 | 106 | 6 hr | 76% |
| 13b | Dimethyl sulfoxide | 22 | 116 | 86 | 6 hr | 75% |
| 13c | N-methyl-2-pyrrolidone | 22 | 86 | 86 | 8 hr | 82% |
| 13d | N,N-dimethylformamide | 44 | 86 | 86 | 6 hr | 54% |
| 13e | N,N-dimethylacetamide | 44 | 86 | 86 | 6 hr | 77% |
| 13f | N,N-dimethylpropanamide | 22 | 86 | 86 | 6 hr | 70% |

Example 14

Synthesis of Norbuprenorphine

Norbuprenorphine can be prepared according to the following reaction scheme:

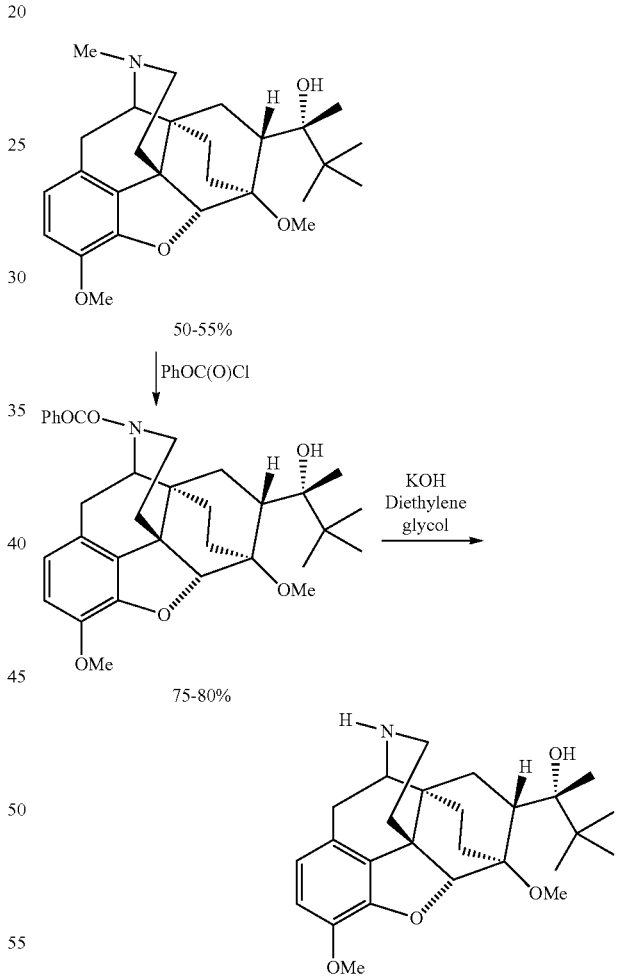

For the first step, N-methyl-3-O-methyl buprenorphine can be contacted with about 1.5-3 equivalents of phenyl chloroformate and about 3-4 equivalents of sodium bicarbonate, and the reaction can be conducted at a temperature of about 20-80° C. For the second step, N-phenoxycarbonyl-3-O-methyl buprenorphine can be contacted with about 6-8 equivalents of KOH and about 7-10 equivalents of diethylene glycol, and the reaction can be conducted at a temperature of about 110-125° C. 3-O-Methyl norbuprenorphine can be isolated from the reaction mixture using standard procedures.

What is claimed is:

1. A process for preparing a compound of Formula (III), the process comprising:
   (a) contacting a compound of Formula (I) with a hydrocarbyl haloformate, $XC(O)OR^{18}$, and a hindered tertiary amine to form a compound of Formula (II); and
   (b) contacting the compound of Formula (II) with a quaternary ammonium salt to form the compound of Formula (III) according to the following reaction scheme:

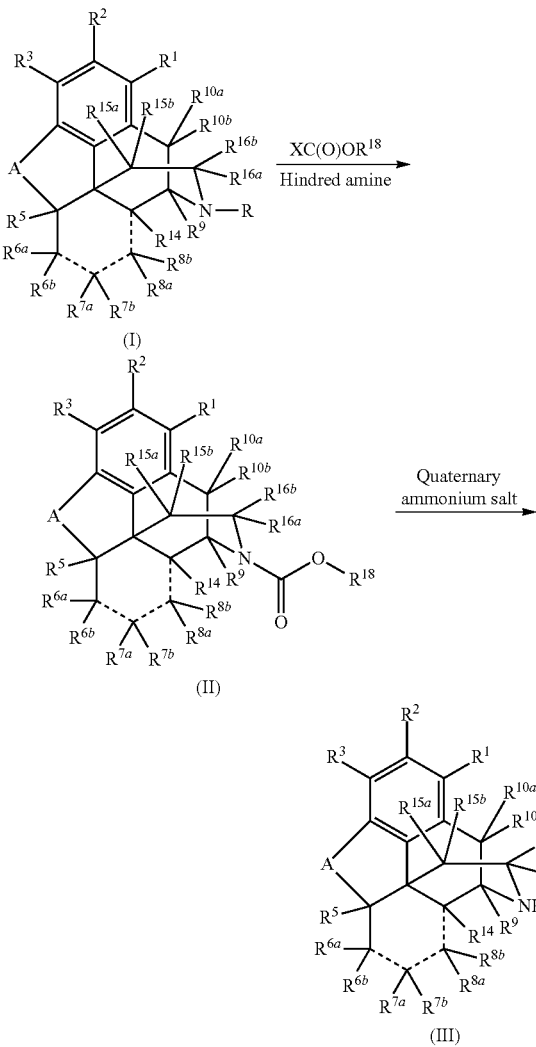

wherein:
A is oxygen;
R is hydrocarbyl or substituted hydrocarbyl;
$R^1$, $R^2$, and $R^3$ are independently hydrogen, amino, halogen, $\{-\}OH$, $\{-\}OR^{1611}$, $\{-\}SH$, $\{-\}SR^{1611}$, $\{-\}NHR^{1611}$, $\{-\}NR^{1611}R^{1612}$, hydrocarbyl, or substituted hydrocarbyl;
$R^5$, $R^{6a}$, $R^{6b}$, $R^{7a}$, $R^{7b}$, $R^{8a}$ $R^{8b}$, $R^9$, $R^{10a}$, $R^{10b}$, $R^{14}$, $R^{15a}$, $R^{15b}$, $R^{16a}$, and $R^{16b}$ are independently hydrogen, amino, halogen, $\{-\}OH$, $\{-\}OR^{1611}$, $\{-\}SH$, $\{-\}SR^{1611}$, $\{-\}NHR^{1611}$, $\{-\}NR^{1611}R^{1612}$, hydrocarbyl, or substituted hydrocarbyl; wherein any pair of $R^{\#a}$ and $R^{\#b}$ wherein # is any one of 6, 7, 8, 10, 15, 16, optionally together form a moiety chosen from $\{=\}O$, $\{=\}S$, $\{=\}CH_2$, $\{=\}NR^{1612}$, or $\{-\}O(CH_2)_nO\{-\}$, wherein n is an integer of 1 or greater;
$R^{18}$ is hydrocarbyl or substituted hydrocarbyl
$R^{1611}$ and $R^{1612}$ are independently hydrocarbyl or substituted hydrocarbyl;
X is halogen ; and
the dashed lines between the carbon atoms at positions 6 and 7, 7 and 8, and 8 and 14 represent carbon to carbon bonds chosen from (a) single bonds between all carbon atoms, wherein optionally one of the $R^6$ pair and $R^{14}$ form an alkano bridge; (b) single bonds between the carbons at both positions 7 and 8 and 8 and 14, and a double bond between the carbons at positions 6 and 7, wherein only one of $R^6$ pair is present; (c) single bonds between the carbons at both positions 6 and 7 and 8 and 14, and a double bond between the carbons at positions 7 and 8, wherein only one of each $R^7$ and $R^8$ pair is present; or (d) double bonds between the carbons at both positions 6 and 7 and 8 and 14, and a single bond between the carbons at positions 7 and 8, wherein only one of each $R^6$, $R^7$, and $R^8$ pair is present and $R^{14}$ is not present.

2. The process of claim 1, wherein R is methyl, cyclopropylmethyl, cyclobutylmethyl, or allyl; $R^3$ is $\{-\}OH$, $\{-\}O$-alkyl, or $\{-\}OR^{1611}$; $R^1$, $R^2$, $R^5$, $R^{8a}$ $R^{8b}$, $R^9$, $R^{10a}$, $R^{10b}$, $R^{15a}$, $R^{15b}$, $R^{16a}$, and $R^{16b}$, if present, are hydrogen; $R^{14}$ is hydrogen, $\{-\}OH$, $\{-\}O$-alkyl, $\{-\}OR^{1611}$, or forms an alkano bridge with one of the $R^6$ pair; and $R^{18}$ is alkyl, halo-substituted alkyl, alkoxyalkyl, alkenyl, aryl, or substituted aryl.

3. The process of claim 2, wherein $R^{6a}$ is $\{-\}OH$, $\{-\}O$-alkyl, $\{-\}OR^{1611}$, or $\{-\}NR^{1611}R^{1612}$, and $R^{6b}$ is hydrogen, or together $R^{6a}$ and $R^{6b}$ form $\{=\}O$, $\{=\}CH_2$, or $\{-\}O(CH_2)_nO\{-\}$, $R^{7a}$ and $R^{7b}$ are hydrogen, and $R^{14}$ is hydrogen, $\{-\}OH$, $\{-\}O$-alkyl, or $\{-\}OR^{1611}$; or $R^{6a}$ is $\{-\}OH$, $\{-\}O$-alkyl, or $\{-\}OR^{1611}$, $R^{6b}$ and $R^{14}$ form an alkano bridge, $R^{7a}$ is alkyl or substituted alkyl, and $R^{7b}$ is hydrogen.

4. The process of claim 1, wherein the hydrocarbyl haloformate is an alkyl haloformate, a halo-substituted alkyl haloformate, an alkenyl haloformate, an alkoxyalkyl haloformate, or an aryl haloformate.

5. The process of claim 1, wherein the hindered tertiary amine is N,N-diisopropylethylamine, N,N-diisopropyl-2-ethylbutylamine; N,N-diisopropyl-3-pentylamine, triisopropylamine, triethylamine, N-ethylpiperidine, or a combination thereof.

6. The process of claim 1, wherein the mole to mole ratio of the compound of Formula (I) to the hydrocarbyl haloformate to the hindered tertiary amine is from about 1:1:1 to about 1:3:3.

7. The process of claim 1, wherein step (a) further comprises an inorganic proton acceptor, the inorganic proton acceptor is an inorganic salt, and the mole to mole ratio of the hindered tertiary amine to the inorganic salt is from about 1:7 to about 1:8.

8. The process of claim 1, wherein step (a) is conducted in the presence of a solvent chosen from dichloromethane, dichloroethane, chloroform, acetonitrile, methyl ethylketone, methyl isobutylketone, toluene, or a combination thereof; the volume to mass ratio of the solvent to the compound of Formula (I) is from about 2:1 to about 20:1; and step (a) is conducted at a temperature from about 20° C. to about 60° C.

9. The process of claim 1, the mole to mole ratio of the compound of Formula (II) to the quaternary ammonium salt is from about 1:20 to about 1:80.

10. The process of claim 9, wherein step (b) is conducted in the presence of a solvent chosen from dimethyl sulfoxide, N-methyl-2-pyrrolidone, N,N-dimethylacetamide, N,N-dimethylformamide, N,N-dimethylpropylamide, or a combination thereof; the volume to mass ratio of the solvent to the compound of Formula (II) is from about 5:1 to about 20:1; and step (b) is conducted at a temperature from about 70° C. to about 100° C.

11. The process of claim 1, wherein steps (a) and (b) are conducted in a single reaction pot without isolation of the compound of Formula (II).

12. The process of claim 1, wherein the compounds of Formulas (I), (II), and (III) independently have an optical activity of (−) or (+); and the configuration of C-5, C-13, C-14, and C-9, respectively, is RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face of the molecule or the beta face of the molecule.

13. The process of claim 1, wherein step (a) is omitted.

14. The process of claim 13, wherein the mole to mole ratio of the compound of Formula (II) to the quaternary ammonium salt is from about 1:20 to about 1:80; the process is conducted in the presence of a solvent chosen from dimethyl sulfoxide, N-methyl-2-pyrrolidone, N,N-dimethylacetamide, N,N-dimethylformamide, N,N-dimethylpropylamide, or a combination thereof; the volume to mass ratio of the solvent to the compound of Formula (II) is from about 5:1 to about 20:1; and the process is conducted at a temperature from about 70° C. to about 100° C.

15. The process of claim 14, wherein $R^3$ is {—}OH, {—}O-alkyl, or {—}$OR^{1611}$; $R^1$, $R^2$, $R^5$, $R^{8a}$ $R^{8b}$, $R^9$, $R^{10a}$, $R^{10b}$, $R^{15a}$, $R^{15b}$, $R^{16a}$, and $R^{16b}$, if present, are hydrogen; $R^{14}$ is hydrogen, {—}OH, {—}O-alkyl, {—}$OR^{1611}$, or forms an alkano bridge with one of the $R^6$ pair; and $R^{18}$ is alkyl, halo-substituted alkyl, alkoxyalkyl, alkenyl, aryl, or substituted aryl.

16. The process of claim 15, wherein $R^{6a}$ is {—}OH, {—}O-alkyl, {—}$OR^{1611}$, or {—}$NR^{1611}R^{1612}$, and $R^{6b}$ is hydrogen, or together $R^{6a}$ and $R^{6b}$ form {=}O, {=}$CH_2$, or {—}$O(CH_2)_nO${—}, $R^{7a}$ and $R^{7b}$ are hydrogen, and $R^{14}$ is hydrogen, {—}OH, {—}O-alkyl, or {—}$OR^{1611}$; or $R^{6a}$ is {—}OH, {—}O-alkyl, or {—}$OR^{1611}$, $R^{6b}$ and $R^{14}$ form an alkano bridge, $R^{7a}$ is alkyl or substituted alkyl, and $R^{7b}$ is hydrogen.

17. The process of claim 13, wherein the compounds of Formulas (II) and (III) independently have an optical activity of (−) or (+); and the configuration of C-5, C-13, C-14, and C-9, respectively, is RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face of the molecule or the beta face of the molecule.

* * * * *